US010568614B2

(12) United States Patent
Sherwinter et al.

(10) Patent No.: US 10,568,614 B2
(45) Date of Patent: Feb. 25, 2020

(54) SYSTEMS AND METHODS FOR FACILITATING CLOSURE OF BODILY OPENINGS

(71) Applicant: COOK MEDICAL TECHNOLOGIES LLC, Bloomington, IN (US)

(72) Inventors: Danny Azriel Sherwinter, Brooklyn, NY (US); John Crowder Sigmon, Jr., High Point, NC (US); Vihar C. Surti, Winston-Salem, NC (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 668 days.

(21) Appl. No.: 15/099,068

(22) Filed: Apr. 14, 2016

(65) Prior Publication Data
US 2016/0228110 A1  Aug. 11, 2016

Related U.S. Application Data
(62) Division of application No. 13/096,433, filed on Apr. 28, 2011.
(Continued)

(51) Int. Cl.
*A61B 17/00* (2006.01)
*A61F 2/00* (2006.01)
*A61B 17/04* (2006.01)

(52) U.S. Cl.
CPC ........ *A61B 17/0057* (2013.01); *A61F 2/0063* (2013.01); *A61B 17/0487* (2013.01);
(Continued)

(58) Field of Classification Search
None
See application file for complete search history.

(56) References Cited

U.S. PATENT DOCUMENTS 3,416,534 A   12/1968   Quinn
4,368,730 A   1/1983   Sharrock
(Continued)

FOREIGN PATENT DOCUMENTS

JP    11-076403    3/1999

OTHER PUBLICATIONS

International Search Report for PCT/US2011/034285 dated Jul. 8, 2011 (6 pgs).
(Continued)

*Primary Examiner* — Shaun L David
(74) *Attorney, Agent, or Firm* — Brinks Gilson & Lione

(57) ABSTRACT

The present embodiments provide a system for facilitating closure of a bodily opening. In one embodiment, the system comprises an anchor having a deployed state dimensioned for engaging tissue surrounding the opening, a first tether coupled to the anchor and extending proximally therefrom, and a graft member comprising a first bore disposed therein. The anchor may comprise a width that is larger than a width of the opening such that the anchor is disposed securely within or distal to the opening. The first tether is dimensioned to be disposed through the first bore in the graft member, such that the graft member is advanced distally over the first tether. The graft member then may be secured to the anchor. Various anchor designs are provided along with a supporting framework that may be coupled to the graft member.

20 Claims, 7 Drawing Sheets

Related U.S. Application Data

(60) Provisional application No. 61/379,243, filed on Sep. 1, 2010, provisional application No. 61/343,435, filed on Apr. 29, 2010.

(52) U.S. Cl.
CPC ............... *A61B 2017/00004* (2013.01); *A61B 2017/00575* (2013.01); *A61B 2017/00579* (2013.01); *A61B 2017/00592* (2013.01); *A61B 2017/00597* (2013.01); *A61B 2017/00601* (2013.01); *A61B 2017/00606* (2013.01); *A61B 2017/00615* (2013.01); *A61B 2017/00619* (2013.01); *A61B 2017/00623* (2013.01); *A61B 2017/00637* (2013.01); *A61B 2017/00676* (2013.01); *A61B 2017/00867* (2013.01); *A61B 2017/00876* (2013.01); *A61B 2017/0496* (2013.01); *A61F 2002/0072* (2013.01)

(56) References Cited

U.S. PATENT DOCUMENTS

| | | |
|---|---|---|
| 4,907,598 A | 3/1990 | Bauer |
| 5,081,997 A | 1/1992 | Bosley, Jr. et al. |
| 5,116,357 A | 5/1992 | Eberbach |
| 5,122,155 A | 6/1992 | Eberbach |
| 5,228,451 A | 7/1993 | Bales et al. |
| 5,258,000 A | 11/1993 | Gianturco |
| 5,308,324 A | 5/1994 | Hammerslag et al. |
| 5,312,435 A | 5/1994 | Nash et al. |
| 5,366,460 A | 11/1994 | Eberbach |
| 5,372,587 A | 12/1994 | Hammerslag et al. |
| 5,397,331 A | 3/1995 | Himpens et al. |
| 5,545,178 A | 8/1996 | Kensey et al. |
| 5,549,633 A | 8/1996 | Evans et al. |
| 5,607,407 A | 3/1997 | Tolkoff et al. |
| 5,662,681 A | 9/1997 | Nash et al. |
| 5,700,277 A | 12/1997 | Nash et al. |
| 5,728,114 A | 3/1998 | Evans et al. |
| 5,743,891 A | 4/1998 | Tolkoff et al. |
| 5,906,594 A | 5/1999 | Scarfone et al. |
| 6,126,633 A | 10/2000 | Kaji et al. |
| 6,210,377 B1 | 4/2001 | Ouchi |
| 6,456,874 B1 | 9/2002 | Hafer et al. |
| 6,689,122 B2 | 2/2004 | Yamamoto |
| 7,488,347 B1 | 2/2009 | Goble et al. |
| 7,897,167 B2 | 3/2011 | Armstrong et al. |
| 8,277,481 B2 | 10/2012 | Kawaura et al. |
| 2003/0004579 A1 | 1/2003 | Rousseau et al. |
| 2004/0049231 A1 | 3/2004 | Hafer et al. |
| 2004/0098044 A1 | 5/2004 | Van de Moer et al. |
| 2005/0070948 A1 | 3/2005 | Kirsteins |
| 2009/0062844 A1 | 3/2009 | Tekulve et al. |
| 2009/0204130 A1 | 8/2009 | Kantsevoy et al. |
| 2009/0204133 A1 | 8/2009 | Melzer et al. |
| 2009/0287229 A1 | 11/2009 | Ogdahl |

OTHER PUBLICATIONS

Written Opinion for PCT/US2011/034285 (6 pgs).
International Preliminary Report on Patentability for PCT/US2011/034285 dated Oct. 30, 2012 (8 pgs).
Communication pursuant to Rules 161(1) and 162EPC for European Patent Application No. 11718857.3 dated Jan. 7, 2013 (2 pgs).
Response to Communication pursuant to Rules (161(1) and 162 EPC for European Patent Application No. 11718857.3 dated Jul. 16, 2013 (15 pgs).

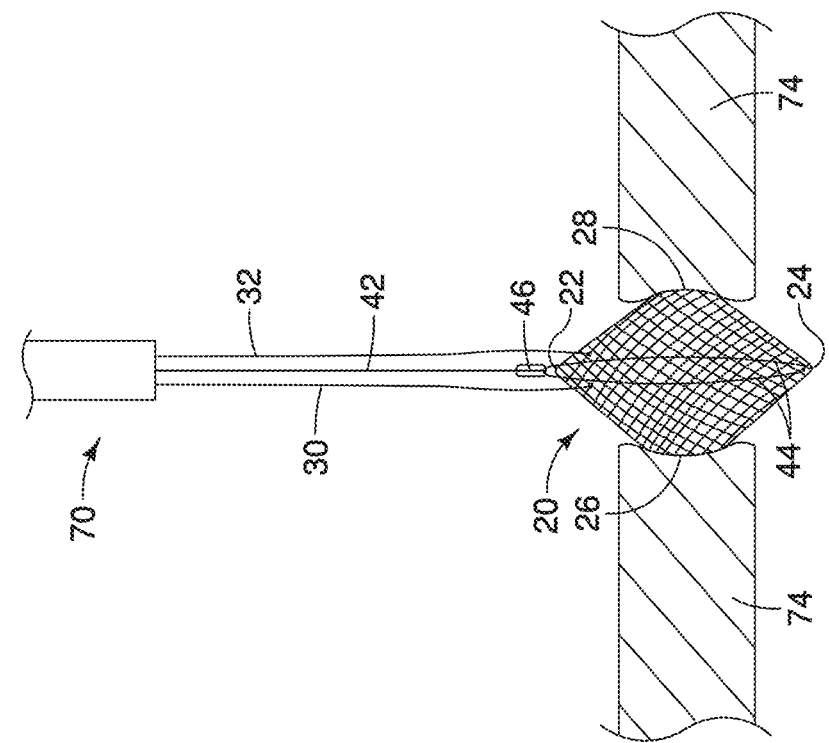
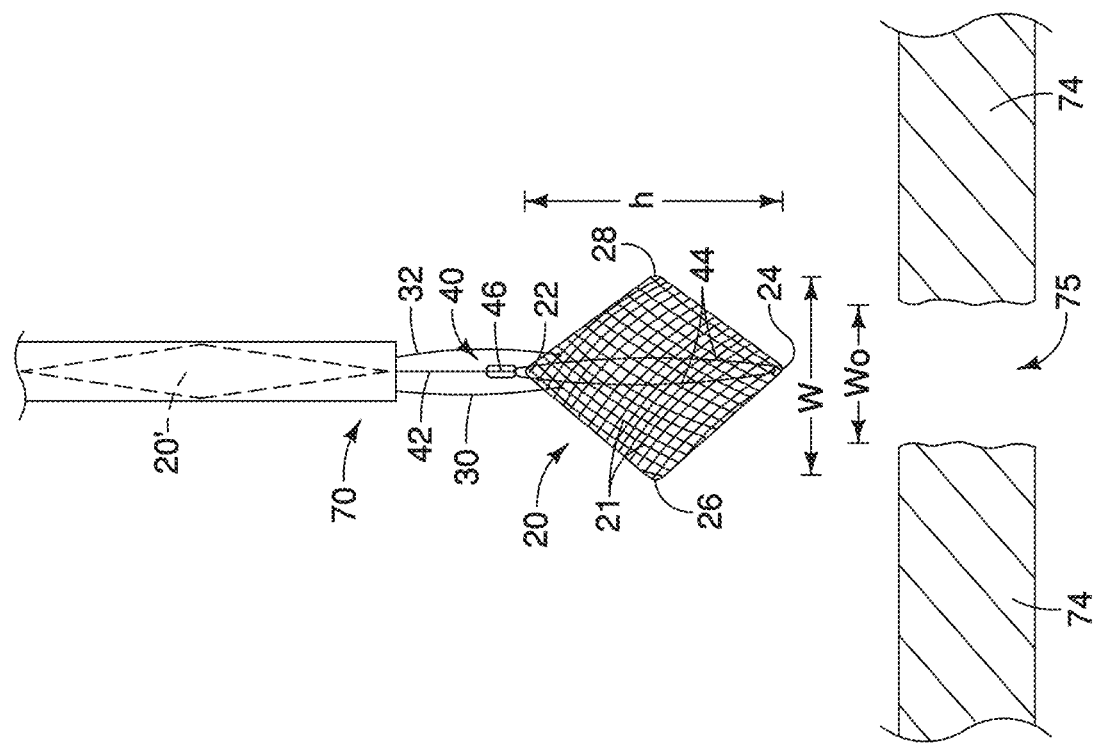

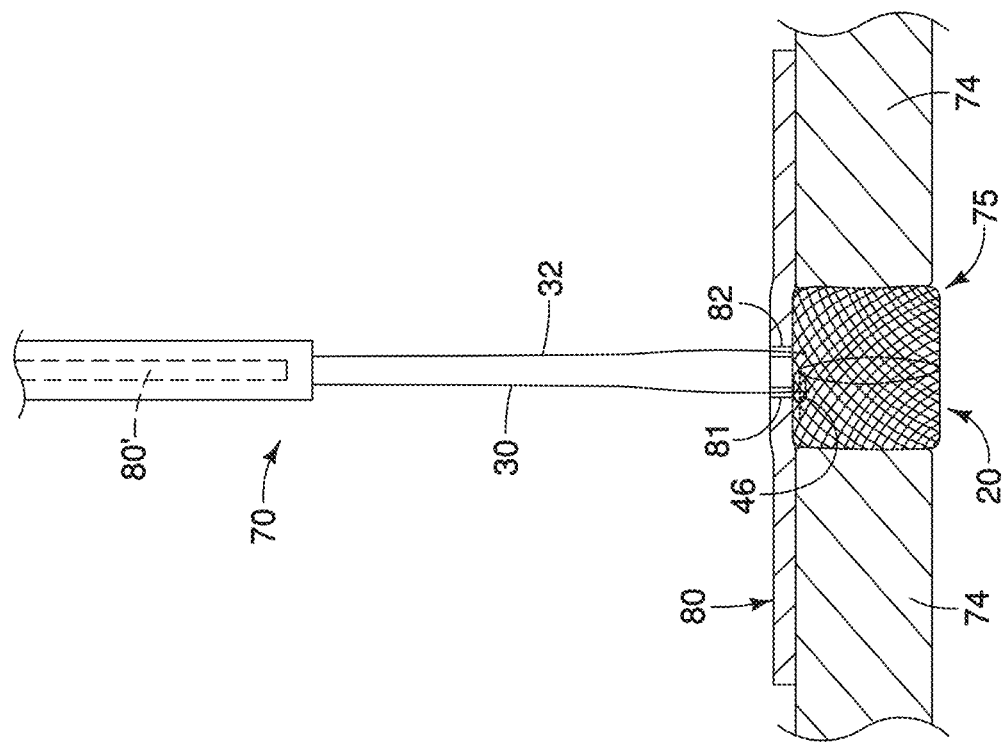
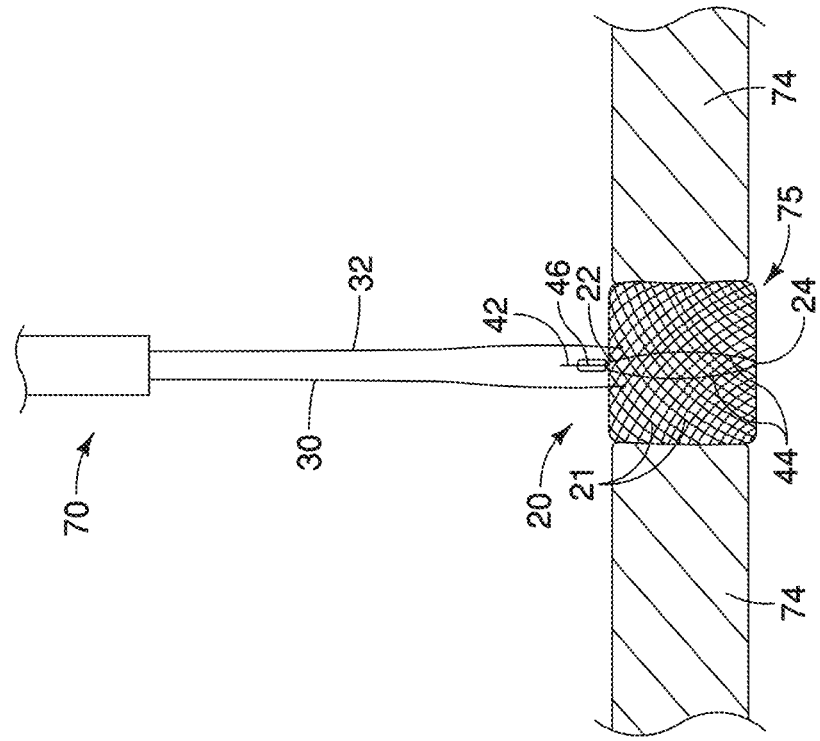

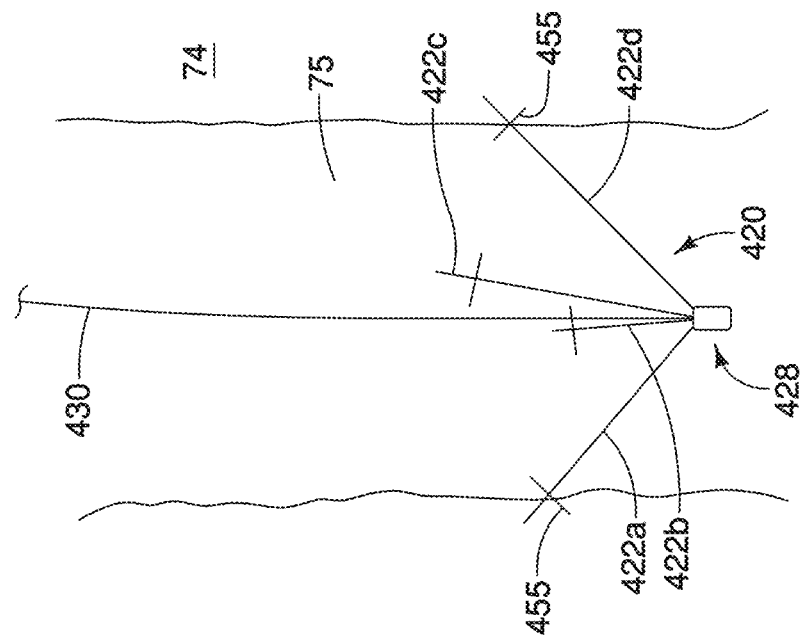
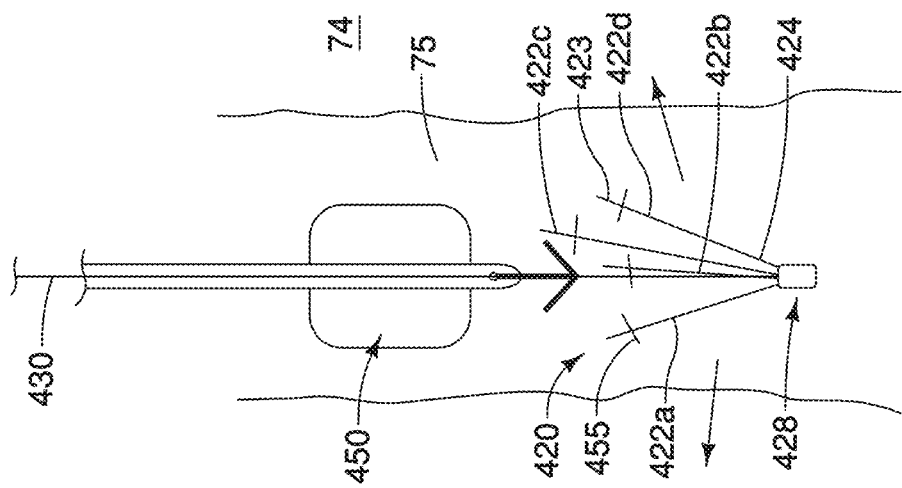

SYSTEMS AND METHODS FOR FACILITATING CLOSURE OF BODILY OPENINGS

PRIORITY CLAIM

This application is a divisional of U.S. patent application Ser. No. 13/096,433, entitled "Systems and Methods for Facilitating Closure of Bodily Openings" filed Apr. 28, 2011, which claims the benefit of U.S. Provisional Application Ser. No. 61/343,435, entitled "Hernia Repair Device, Deployment Device And Technique For The Repair Of Hernias," filed Apr. 29, 2010, and also claims the benefit of U.S. Provisional Application Ser. No. 61/379,243, entitled "Systems and Methods for Facilitating Closure of Bodily Openings," filed Sep. 1, 2010, all of which are hereby incorporated by reference in their entireties.

BACKGROUND

The present embodiments relate generally to medical devices, and more particularly, to systems and methods for closure of bodily openings.

Perforations in tissue or bodily walls may be formed intentionally or unintentionally. For example, an unintentional abdominal hernia may be formed in the abdominal wall due to heavy lifting, coughing, strain imposed during a bowel movement or urination, fluid in the abdominal cavity, or other reasons. Intentional perforations may be formed, for example, during surgical procedures such as translumenal procedures. In a translumenal procedure, one or more instruments, such as an endoscope, may be inserted through a visceral wall, such as the stomach wall. During a translumenal procedure, a closure instrument may be used to close the perforation in the visceral wall. Depending on the structure comprising the perforation, it may be difficult to adequately close the perforation and prevent leakage of bodily fluids.

Attempts to seal perforations have been attempted by coupling a graft member to tissue. For example, during hernia repair, a graft material such as a mesh or patch may be disposed to cover the perforation. The graft material may completely overlap with the perforation, and the edges of the graft material may at least partially overlap with tissue surrounding the perforation. The graft material then may be secured to the surrounding tissue in an attempt to effectively cover and seal the perforation.

In order to secure the graft material to the surrounding tissue, sutures commonly are manually threaded through the full thickness of the surrounding tissue. In the case of an abdominal hernia, the sutures may be threaded through the thickness of the abdominal wall, then tied down and knotted. However, such manual suturing techniques may be time consuming and/or difficult to perform.

There is also a hernia repair method commonly referred to as a "mesh plug" or "plug and patch" repair technique, in which a surgeon uses a mesh plug to fill the perforation. Potential advantages include fewer sutures and less tissue dissection. However, a mesh plug alone may not effectively cover the entire area of the perforation, or alternatively, the mesh plug may shrink, become loose, or poke into the bladder or intestines.

SUMMARY

The present embodiments provide a system for facilitating closure of a bodily opening. In one embodiment, the system comprises an anchor having a deployed state dimensioned for engaging tissue surrounding the opening, a first tether coupled to the anchor and extending proximally therefrom, and a graft member comprising a first bore disposed therein. The anchor may comprise a width that is larger than a width of the opening such that the anchor is disposed securely within or distal to the opening. The first tether is dimensioned to be disposed through the first bore in the graft member, such that the graft member can be advanced distally over the first tether. The graft member then may be secured to the anchor.

In one embodiment, the anchor comprises a plug of material including a plurality of filaments. The plug of material may comprise a diamond shape in a pre-deployment state, and a deployed state having an increased width relative to the pre-deployment state. In an alternative embodiment, the anchor comprises a plurality of deployable members that are biased radially outward in the deployed state.

In other embodiments, the system may further comprise a supporting framework coupled to the graft member, wherein the supporting framework comprises a plurality of deployable members. The supporting framework may comprise a plurality of eyelets, and the graft member may be sutured to the supporting framework around at least one of the eyelets.

The system may comprise a second tether coupled to the anchor, where the first tether is disposed through the first bore in the graft member and the second tether is disposed through a second bore in the graft member. The graft member may be advanced over the first and second tethers toward the anchor, and the first and second tethers are tied together to secure the graft member to the anchor.

Advantageously, an enhanced anchor and graft member attachment may be achieved to better treat the opening. For example, the anchor is capable of expanding to securely engage the opening. Additionally, the expanded anchor is secured to the graft member in a manner that may reduce the rate of migration of the anchor.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIGS. 1-5 are side-sectional views illustrating exemplary method steps that may be used to facilitate closure of an opening using a system according to a first embodiment comprising an anchor and a graft member.

FIGS. 12-13 illustrate an alternative anchor in two different states.

DETAILED DESCRIPTION OF THE PREFERRED EMBODIMENTS

Figure 5:
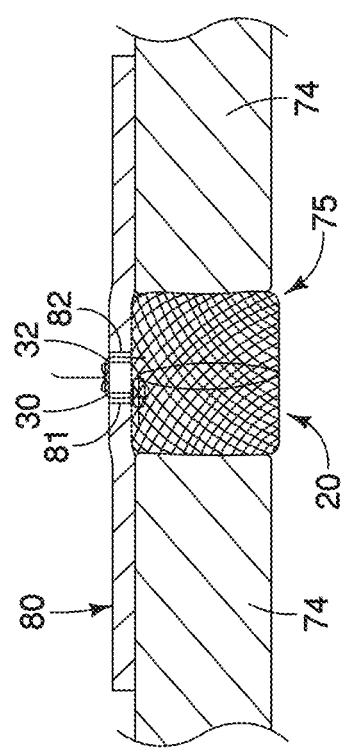

In the present application, the term "proximal" refers to a direction that is generally towards a physician during a medical procedure, while the term "distal" refers to a direction that is generally towards a target site within a patent's anatomy during a medical procedure. Thus, "proximal" and "distal" portions of a device or bodily region may depend on the point of entry for the procedure (e.g., percutaneously versus laparoscopically or endoscopically).

Referring now to FIGS. 1-5, systems and methods are described for facilitating closure of a bodily opening according to a first embodiment. The system comprises an anchor 20, which has pre-deployment and deployed states. In the pre-deployment state, the anchor 20 comprises a generally diamond shape having a proximal region 22, a distal region 24, and side regions 26 and 28, and further comprising a height h and a width w, as shown in FIG. 1. In this example, the anchor 20 may be formed of a plug of material, such as a plurality of filaments 21 that are woven together in a manner that allows compression of the filaments with respect to each other when a sufficient force is applied. In one embodiment, in the pre-deployment state the height h between the proximal and distal regions 22 and 24 may be about the same or greater than the width w between the side regions 26 and 28. Preferably, the width w of the anchor 20 in the pre-deployment state is greater than a width $w_O$ of an opening 75 formed in tissue 74. As will be explained further below, by oversizing the width w of the anchor 20 relative to the width $w_O$ of the opening 75, the anchor 20 may be frictionally held in place within the opening 75. Moreover, the width w of the anchor 20 may be further increased in the deployed state using an actuator 40, as explained further in FIG. 3 below, to further enhance the frictional engagement with the tissue 74 surrounding the opening 75.

The anchor 20 can be fashioned from absorbable and non-absorbable mesh or biologic implant with or without spars of absorbable or non-absorbable material to help it retain its shape and anchorage. The mesh can be shaped like an umbrella or diamond. The deployed expanded shape can be maintained with suture material or a locking mechanism or through the inherent shape and orientation of the spars. In addition, the anchor 20 can be fashioned out of absorbable or non-absorbable spars or a metallic material (e.g., nitinol, stainless steel etc.) shaped as an umbrella, diamond or any shape that expands in diameter after deployment which can be deformed and compressed when placed into the deployment instrument and will then return to its expanded shape after deployment in the defect. In addition, legs of the anchor 20 can have small hooks or tines at the ends to catch on the surrounding tissue. The anchor can be made in multiple sizes for different depth and/or diameter defects.

The system further comprises a first tether 30 coupled to the anchor 20 and extending proximally therefrom, as shown in FIGS. 1-5. The first tether 30 is sized to be disposed through a first bore 81 in a graft member 80, thereby enabling distal advancement of the graft member 80 over the first tether 30 towards the anchor 20 after the anchor 20 has been deployed within the opening 75, as explained further in FIGS. 4-5 below. Optionally, a second tether 32 similarly may be coupled to the anchor 20, and disposed through a second bore 82 in the graft member 80. After distal advancement of the graft member 80 over the first and second tethers 30 and 32 toward the anchor 20, the first and second tethers 30 and 32 may be tied, thereby securing the graft member 80 in place relative to the anchor 20, as explained further in FIG. 5 below. In one example, the first and second tethers 30 and 32 each comprise monofilament sutures, though they can comprise single fibers or woven fibers, may be biodegradable, and have other suitable characteristics to perform the functions herein.

Optionally, the system may comprise an actuator 40 for laterally expanding the anchor 20 between the pre-deployment and the deployed states. In one example, the actuator 40 comprises a suture 42 having a distal region comprising a loop member 44, which may extend around the distal region 24 of the anchor 20 as shown in FIG. 1. The loop member 44 is coupled to a tensioning member 46 that is disposed adjacent to the proximal region 22 of the anchor 20. In use, the tensioning member 46 may be advanced distally over the suture 42 to reduce the overall diameter of the loop member 44, thereby moving the proximal region 22 towards the distal region 24 to reduce the height h, while increasing the width w between the side regions 26 and 28, as explained further in FIG. 3 below.

In the example shown, the opening 75 is a hernia located in the tissue 74 of the abdominal wall. While treatment of a hernia is shown for illustrative purposes, it will be apparent that the systems described herein may be used in a wide range of medical procedures, including but not limited to any exemplary procedures described herein.

The initial stages of the hernia repair may be performed using various techniques, for example, an open technique, a laparoscopic technique, an endoscopic technique, or a percutaneous technique. In an open technique, an incision may be made in the abdominal wall and the hernia may be repaired using generally known principles.

In a laparoscopic technique, two or three smaller incisions may be made to access the hernia site. A laparoscope may be inserted into one incision, and surgical instruments may be inserted into the other incision(s) and the hernia may be repaired in a similar fashion as the open procedure.

In an endoscopic technique, an endoscope is used instead of the laparoscopic devices, and no visible incisions may be made on the skin of the patient. In particular, the endoscope may be advanced through a bodily lumen such as the alimentary canal, with an access hole being created through the alimentary canal, to obtain peritoneal access to the hernia. One or more components, such as an insertion tool, may be advanced through a working lumen of the endoscope. The distal end of the insertion tool may be viewed via optical elements of the endoscope, which may comprise fiber optic components for illuminating and capturing an image distal to the endoscope.

The percutaneous approach is similar to the laparoscopic approach, however, in the percutaneous approach an insertion tool may be advanced directly through a patient's abdominal skin. In particular, with the components loaded, the insertion tool is advanced directly through the abdominal skin, through the tissue, and may be advanced just distal to the opening and into the peritoneum. In order to optimally visualize the insertion tool, a laparoscopic viewing device may be positioned in the peritoneum, or an endoscope may be translumenally advanced in proximity to the target site, as noted above. Alternatively, the insertion tool and markers disposed thereon may be viewed using fluoroscopy of other suitable techniques.

After gaining access to the opening 75 using any of the above-referenced techniques, an insertion tool 70, such as a catheter or a needle, may be used to delivery one or more of the components of the system. If a needle is used, it may be an endoscopic ultrasound (EUS) or echogenic needle, such as the EchoTip® Ultrasound Needle, or the EchoTip® Ultra Endoscopic Ultrasound Needle, both manufactured by Cook Endoscopy of Winston-Salem, N.C.

The anchor 20 is disposed within a lumen of the insertion tool 70, as illustrated in the dashed delivery state 20' of the anchor, shown in FIG. 1. The anchor may be advanced within the lumen of the insertion tool 70, e.g., using a stylet, and then is ejected from a distal end of the insertion tool 70. The anchor 20 assumes its pre-deployment state, as shown in FIG. 1. At this time, the first and second tethers 30 and 32, along with the suture 42 of the actuator 40, each extend proximally through the lumen of the insertion tool 70 for manipulation by a physician.

Referring to FIG. 2, the anchor 20 is advanced distally by a suitable device, such as a pusher tube, insertion tool, forceps or other grasping instrument. The anchor 20 is positioned within the opening 75, as shown in FIG. 2. Advantageously, the anchor 20 is diamond-shaped in the pre-deployment state, such that the distal region 24 is tapered to facilitate entry into the opening 75. Since the width w of the anchor 20 preferably is greater than the width $w_O$ of the opening 75 in the pre-deployment state, a force may be applied, e.g., using the pusher tube, insertion tool, forceps or other grasping instrument, to urge the anchor 20 in place so that at least the side regions 26 and 28 securely engage the tissue 74 surrounding the opening 75, as shown in FIG. 2. Alternatively, the anchor 20 may be deployed distal to the opening 75, in which case the anchor can assume a diameter larger than the opening 75 and provide anchoring functionality just distal to the tissue 74 with the same method steps otherwise being performed as shown herein.

Referring to FIG. 3, in a next step the actuator 40 is actuated to laterally expand the anchor 20, thereby further securing the anchor 20 within the opening 75 and/or distal to the opening 75. In particular, the tensioning member 46 is advanced distally over the suture 42 to reduce the overall diameter of the loop member 44, thereby moving the proximal region 22 towards the distal region 24 to reduce the height h, while increasing the width w between the side regions 26 and 28 of the anchor 20 to enhance a secure fit between the side regions 26 and 28 of the anchor 20 and the tissue 74 surrounding the opening 75. An increased width w of the anchor 20 in the deployed state of FIG. 3 may provide an increased frictional engagement with tissue disposed within the opening 75.

Preferably, the tensioning member 46 comprises a one-way movement feature, such as a cinching or ratcheting mechanism, to prevent proximal movement of the tensioning member 46 relative to the anchor 20 after deployment. Alternatively, the tensioning member 46 may comprise a rubber disc or beaded member, which may frictionally engage an exterior surface of the suture 42, but may be advanced distally over the suture 40 with a suitable external force. After actuating the actuator 40, the suture 42 may be cut by a suitable device, such as laparoscopic scissors, leaving the anchor 40 in place as shown in FIG. 3.

Referring to FIGS. 4-5, in a next step the graft member 80 may be advanced distally over the first and second tethers 30 and 32 towards the anchor 20. Properties of suitable graft members 80 are described in detail below. The graft member 80 comprises first and second bores 81 and 82, as noted above, which are sized to permit advancement of the graft member 80 over the first and second tethers 30 and 32, respectively.

In use, proximal ends of the first and second tethers 30 and 32 are disposed through the first and second bores 81 and 82 of the graft member 80 outside of the patient, and the graft member 80 is advanced distally relative to the first and second tethers 30 and 32. The graft member 80 may be delivered through the insertion tool 70, as depicted by the dashed lines of a graft member 80' in the delivery state in FIG. 4. Alternatively, the graft member 80 may be delivered directly through a trocar, e.g., a 5 mm trocar. When ejected from the insertion tool 70 or the trocar, the graft member 80 then is positioned in place relative to the tissue 74 using a suitable grasping device, or a pusher tube or the insertion tool 70 itself, such that the graft member 80 is adjacent to the tissue 74 and covering the opening 75, as shown in FIG. 4.

In a next step, a suture tying device may be used to tie the first and second tethers 30 and 32 together in a manner that secures the graft member 80 adjacent to the tissue 74 and the anchor 20. By way of example, and without limitation, one suitable suture tying device is disclosed in U.S. patent application Ser. No. 12/125,525, filed May 22, 2008, the disclosure of which is hereby incorporated by reference in its entirety. Another suitable suture tying device is disclosed in U.S. patent application Ser. No. 12/191,001, filed Aug. 13, 2008, the disclosure of which is hereby incorporated by reference in its entirety. Upon completion of the tying procedure, the first and second tethers 30 and 32 may be cut by a suitable device, such as laparoscopic scissors, leaving the anchor 40 and the graft member 80 in place as shown in FIG. 5.

Advantageously, using the anchor 20, the first and second tethers 30 and 32, and the graft member 80 in combination, along with the techniques described, an enhanced anchor and graft member attachment may be achieved to comprehensively treat the opening 75. In this example, the anchor 20 is capable of expanding to fill the opening 75, potentially resulting in better tissue ingrowth and lower rates of recurrence. Moreover, the anchor 20 is secured within the opening 75 in an expanded, secure manner that may reduce anchor migration. Further, the coupling of the anchor 20 to the graft member 80 provides an enhanced seal relative to a plug alone, and the secure attachment of the anchor 20 to the graft member 80 may further reduce the rate of migration of the anchor 20.

The graft member 80 may comprise any suitable material for covering the opening 75 and substantially or entirely inhibiting the protrusion of abdominal matter. In one embodiment, the graft member 80 may comprise small intestinal submucosa (SIS), such as BIODESIGN® SURGISIS® Tissue Graft, available from Cook Biotech, Inc., West Lafayette, Ind., which provides smart tissue remodeling through its three-dimensional extracellular matrix (ECM) that is colonized by host tissue cells and blood vessels, and provides a scaffold for connective and epithelial tissue growth and differentiation along with the ECM components. The graft member 80 may be lyophilized, or may comprise a vacuum pressed graft that is not lyophilized. In one example, the graft member 80 would be a one to four layer lyophilized soft tissue graft made from any number of tissue engineered products. Reconstituted or naturally-derived collagenous materials can be used, and such materials that are at least bioresorbable will provide an advantage, with materials that are bioremodelable and promote cellular invasion and ingrowth providing particular advantage. Suitable bioremodelable materials can be provided by collagenous ECMs possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. The graft member 80 may also comprise a composite of a biomaterial and a biodegradable polymer. Additional details may be found in U.S. Pat. No. 6,206,931 to Cook et al., the disclosure of which is incorporated herein by reference in its entirety.

Figure 7:
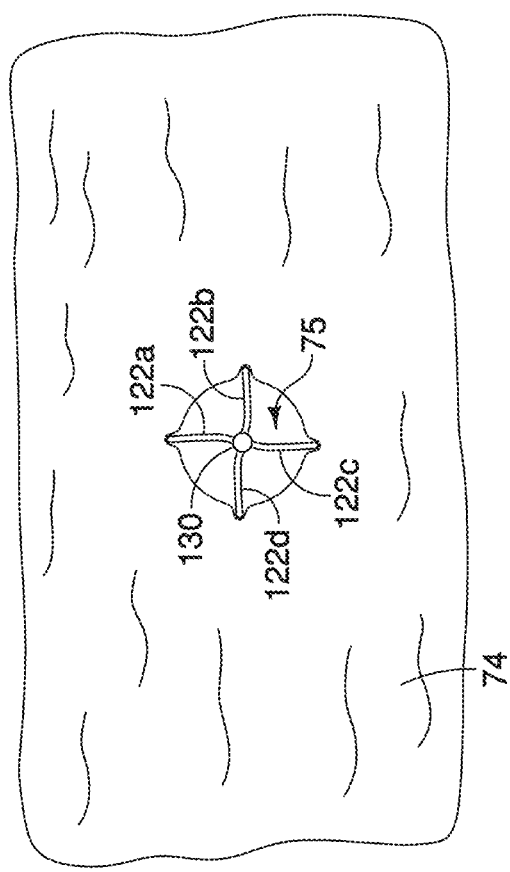
FIG. 7 is a top view illustrating use of the alternative anchor of FIG. 6.
Figure 6:
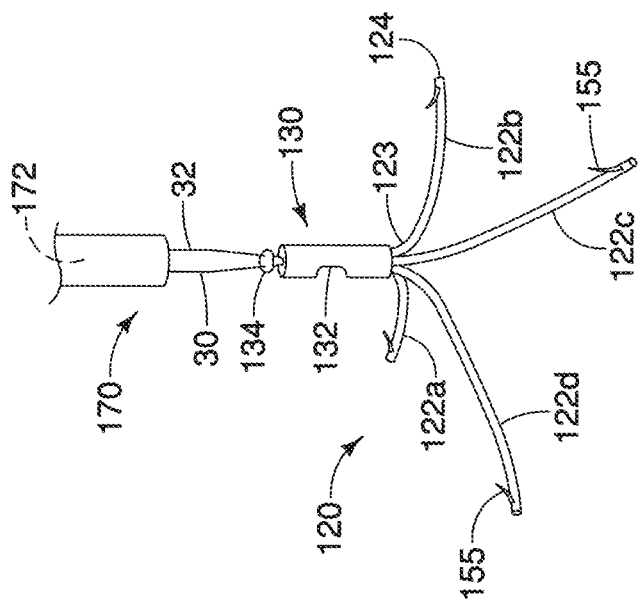
FIG. 6 is an elevated perspective view of an alternative anchor.

Referring now to FIGS. 6-7, an alternative anchor 120 is shown and described. The anchor 120 comprises a plurality of deployable members 122a-122d, each having a proximal end 123 and a distal end 124. One or more barbs 155 may be provided on one or multiple deployable members 122a-122d, and in the example of FIG. 6, a single barb 155 is formed near the distal ends 123 of each deployable member 122a-122d. The plurality of deployable members 122a-122d extend distally from a retaining member 130. One or more tethers, such as first and second tethers 30 and 32 of FIGS. 1-5, may be coupled to the anchor 120, e.g., directly around the retaining member 130 or attached to an eyelet 134 at the proximal end of the anchor 120.

In addition to the expanded deployed state shown in FIG. 6, the anchor 120 comprises a delivery state in which the anchor 120 may be delivered through a suitable insertion tool 170, such as a catheter or needle, as described above. As noted above, in the delivery state the plurality of deployable members 122a-122d are generally parallel to one another, with the distal ends 124 being closer together and facing distally within the insertion tool 170.

In a preferred embodiment, each of the plurality of deployable members 122a-122d the anchor 20 comprises a shape-memory material, such as a nickel-titanium alloy (nitinol). If a shape-memory material such as nitinol is employed, the plurality of deployable members 122a-122d may be manufactured such that they can assume the preconfigured expanded state shown in FIG. 6 upon application of a certain cold or hot medium. More specifically, a shape-memory material may undergo a substantially reversible phase transformation that allows it to "remember" and return to a previous shape or configuration. For example, in the case of nitinol, a transformation between an austenitic phase and a martensitic phase may occur by cooling and/or heating (shape memory effect) or by isothermally applying and/or removing stress (superelastic effect). Austenite is characteristically the stronger phase and martensite is the more easily deformable phase.

In an example of the shape-memory effect, a nickel-titanium alloy having an initial configuration in the austenitic phase may be cooled below a transformation temperature $(M_f)$ to the martensitic phase and then deformed to a second configuration. Upon heating to another transformation temperature $(A_f)$, the material may spontaneously return to its initial, predetermined configuration, as shown in FIG. 6. Generally, the memory effect is one-way, which means that the spontaneous change from one configuration to another occurs only upon heating. However, it is possible to obtain a two-way shape memory effect, in which a shape memory material spontaneously changes shape upon cooling as well as upon heating.

Alternatively, the plurality of deployable members 122a-122d may be made from other metals and alloys that are biased, such that they may be restrained prior to deployment, but are inclined to return to their relaxed, expanded configuration upon deployment. Solely by way of example, the plurality of deployable members 122a-122d may comprise other materials such as stainless steel, cobalt-chrome alloys, amorphous metals, tantalum, platinum, gold and titanium, or may be made from non-metallic materials, such as thermoplastics and other polymers.

The anchor 120 is disposed within a lumen 172 of the insertion tool 170 in the delivery state, i.e., with the plurality of deployable members 122a-122d being generally parallel to one another. In the delivery state, the distal ends 124 of each of the plurality of deployable members 122a-122d are positioned proximal to the distal end of the insertion tool 170. In the delivery state, the plurality of deployable members 122a-122d are generally parallel to one another, with the distal ends 124 being closer together. Moreover, the distal ends 124 of the anchor 120 preferably face distally within the insertion tool 170 in the delivery state.

In use, the insertion tool 170 is positioned such that its distal end is within the opening 75. In this embodiment, the distal tip of the insertion tool 170 must be inserted within the opening 75 to properly deploy the self-expanding anchor 120 therein. Optionally, the insertion tool 170 may comprise a flexible distal tip feature, such as a spring coil that may be flexed by retracting a stylet coupled to it, to maneuver the distal tip of the insertion tool 170 into an angle suitable for insertion into the opening 75.

After positioning of the insertion tool 170, the anchor 120 and the insertion tool 170 are translated relative to one another to eject the anchor 120 from the insertion tool 170. A suitable device, such as a stylet, torque cable or spring coil, may be disposed for longitudinal movement within the lumen 172 of the insertion tool 170 to permit translation of the anchor 120 relative to the insertion tool 170. Optionally, the retaining member 130 may comprise a notch 132 or other feature for engaging the stylet, torque cable or spring coil within the lumen 172 prior to ejection of the anchor 120.

Upon ejection from the insertion tool 170, the plurality of deployable members 122a-122d assume the expanded deployed shape, in which each deployable member 122a-122d engages the tissue 74 surrounding the opening 75, as shown in FIG. 7. The plurality of deployable members 122a-122d are oversized relative to the opening 75 to ensure a secure engagement with the tissue 74. In particular, an overall width of the anchor 120 in the expanded state, measured as the longitudinal distance between the distal end 124 of the deployable member 122a and the distal end 124 of the opposing deployable member 122c, is greater than the width $w_O$ of the opening 75. Moreover, the barbs 155 on each of the deployable members 122a-122d may promote a secure attachment to the tissue 74.

With the anchor 120 deployed securely within the opening 75, in a next step the graft member 80 is advanced distally over the first and second tethers 30 and 32 towards the anchor 120, as generally described above in FIGS. 4-5. A suture tying device may be used to tie the first and second tethers 30 and 32 together in a manner that holds the graft member 80 adjacent to the tissue 74 and the anchor 120, as explained above. Upon completion of the tying procedure, the first and second tethers 30 and 32 may be cut off, leaving the anchor 120 and the graft member 80 in place. Notably, in the embodiment of FIGS. 6-7, the anchor 120 does not plug the entire opening 75, but rather is intended to provide a secure anchor into the tissue 74 that may be used in conjunction with the graft member 80. Since the deployable members 122a-122d are oversized relative to the opening 75, anchor migration may be reduced.

Figure 9:
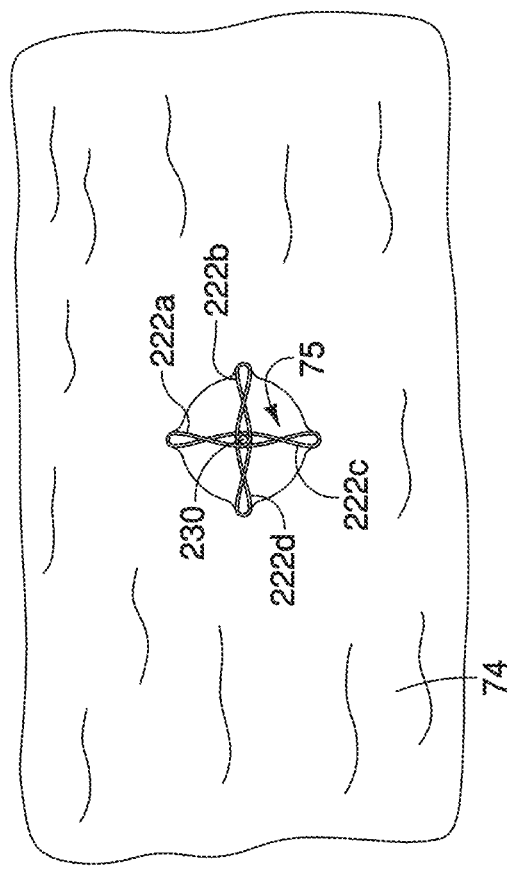
FIG. 9 is a top view illustrating use of the alternative anchor of FIG. 8.
Figure 8:
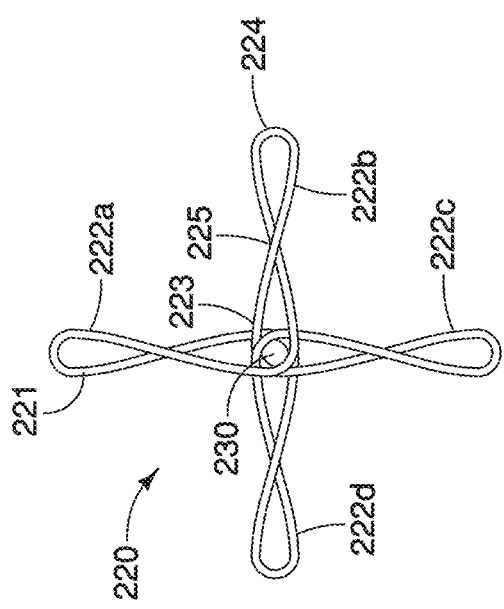
FIG. 8 is top view of a further alternative anchor.

Referring now to FIGS. 8-9, a further alternative anchor 220 is shown and described. The anchor 220 comprises a plurality of deployable members 222a-222d, each having a proximal end 223 and a distal end 224. The anchor 220 may be formed of a single wire 221, or a plurality of wires, that are bent in the configuration shown in FIG. 8, whereby the plurality of deployable members 222a-222d extend distally from a central portion 230. Notably, each of the distal ends 224 of the plurality of deployable members 222a-222d comprises generally curved apices. Further, each of the distal ends 224 of the plurality of deployable members 222a-222d may comprise an overlap region 225 where the wire crosses over itself, as shown in FIG. 8. One or more tethers, such as first and second tethers 30 and 32 of FIGS. 1-5, may be coupled to the anchor 220, preferably tied around the central portion 230 of the wire 221.

In addition to the expanded deployed state shown in FIG. 8, the anchor 220 comprises a delivery state in which the anchor 220 may be delivered through the insertion tool 170 described in FIG. 6 above. In the delivery state, the plurality of deployable members 222a-222d are generally parallel to one another, with the distal ends 224 being closer together. Moreover, the distal ends 224 of the anchor 220 preferably face distally within the insertion tool 170 in the delivery state. In a preferred embodiment, each of the plurality of deployable members 222a-222d of the anchor 220 comprises a shape-memory material, such as a nickel-titanium alloy (nitinol), or alternatively other metals and alloys that are biased, such that they may be restrained prior to deployment, but are inclined to return to their relaxed, expanded configuration upon deployment.

In use, the insertion tool 170 is positioned such that its distal end is within the opening 75, as described above. The anchor 220 is disposed within the lumen 172 of the insertion tool 170 in the delivery state, with the plurality of deployable members 222a-222d being generally parallel to one another, and the distal ends 224 of each of the plurality of deployable members 222a-222d proximal to the distal end of the insertion tool 170. Then, the insertion tool 170 and the anchor 220 are translated relative to one another to eject the anchor 220 from the insertion tool.

Upon ejection from the insertion tool 170, the plurality of deployable members 222a-222d assume the expanded deployed shape, in which each deployable member 222a-222d engages the tissue 74 surrounding the opening 75, as shown in FIG. 9. The plurality of deployable members 222a-222d are oversized relative to the opening 75 to ensure a secure engagement with the tissue 74. In particular, an overall width of the anchor 220 in the expanded state, measured as the longitudinal distance between the distal end 224 of the deployable member 222a and the distal end 224 of the opposing deployable member 222c, is greater than the width $w_O$ of the opening 75.

With the anchor 220 deployed securely within the opening 75, in a next step the graft member 80 is advanced distally over the first and second tethers 30 and 32 towards the anchor 220, as generally described above in FIGS. 4-5 and FIGS. 5-6 above, and a suture tying device may be used to tie the first and second tethers 30 and 32 together in a manner that holds the graft member 80 adjacent to the tissue 74 and the anchor 220. Like the embodiment of FIGS. 6-7, the anchor 220 does not plug the entire opening 75, but rather is intended to provide a secure anchor into the tissue 74 that may be used in conjunction with the graft member 80.

Figure 11:
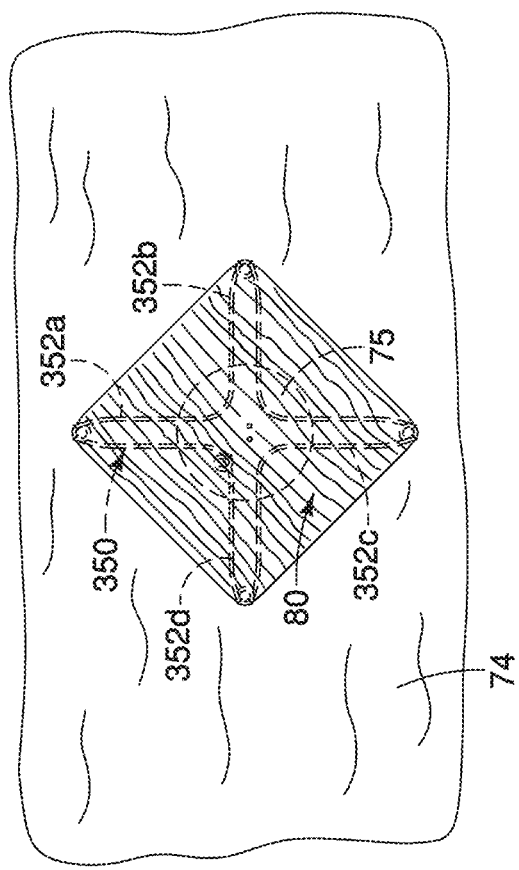
FIG. 11 is a top view illustrating use of the graft member and the supporting framework of FIG. 10.
Figure 10:
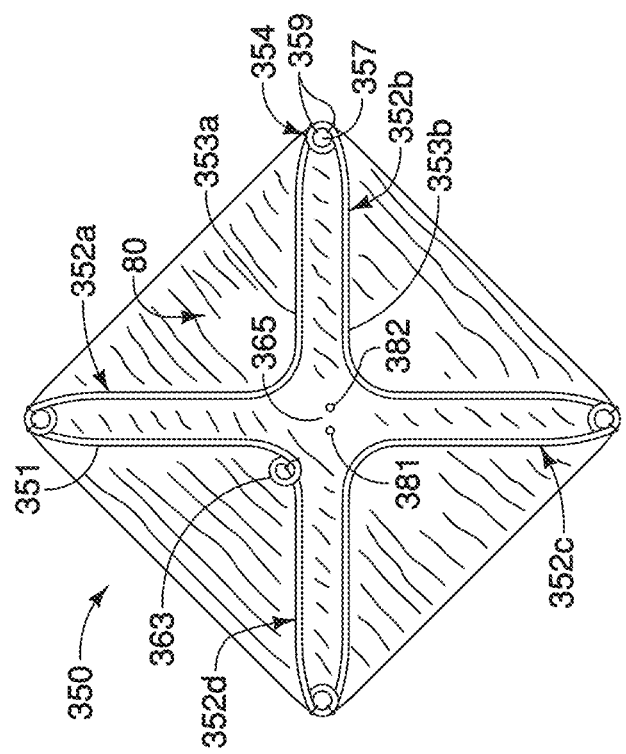
FIG. 10 is bottom view of a graft member and a supporting framework.

Referring now to FIGS. 10-11, a supporting framework 350, which may be coupled to the graft member 80, is shown and described. The supporting framework 350 comprises a plurality of deployable members 352a-352d, each having a proximal end with first and second segments 353a and 353b, and a distal end 354. The supporting framework 350 may be formed of a single wire 351, or a plurality of wires, that are bent in the configuration shown in FIG. 10, whereby the plurality of deployable members 352a-352d extend distally from a central portion 365. Notably, each of the distal ends 354 comprises an eyelet 357, which may be formed where the wire 351 loops over itself. Additionally, an eyelet 363 may be formed in a region where the deployable member 352a transitions into the deployable member 352d, as shown in FIG. 10. The graft member 80 is coupled to the supporting framework 350 using sutures 359, which preferably are looped around each of the eyelets 357 of the deployable members 352a-352d, as well as the eyelet 363.

In addition to the expanded deployed state shown in FIG. 10, the supporting framework 350 comprises a delivery state, in which the supporting framework 350 may be delivered through the insertion tool 170 as described above, or alternatively, directly though a trocar. In the delivery state, the plurality of deployable members 352a-352d are generally parallel to one another. In a preferred embodiment, each of the plurality of deployable members 352a-352d comprises a shape-memory material, such as a nickel-titanium alloy (nitinol), or alternatively other metals and alloys that are biased, such that they may be restrained prior to deployment, but are inclined to return to their relaxed, expanded configuration upon deployment, as described above.

In use, one of the anchors 20, 120 or 220 is positioned and deployed securely within the opening 75, as described in detail above. The first and second tethers 32 and 34 extend away from the anchor that is deployed within the opening 75. The graft member 80 comprises first and second bores 381 and 382, which permit advancement of the graft member 80 over the first and second tethers 30 and 32, as described above.

The graft member 80 is advanced over the first and second tethers 30 and 32 with each of the plurality of deployable members 352a-352d of the supporting framework 350 in the compressed delivery state. The plurality of deployable members 352a-352d are generally parallel to one another, preferably with the distal ends 354 of each of the plurality of deployable members 352a-352d facing proximally. Then, the selected anchor 20, 120 or 220 is ejected from the insertion tool, allowing the plurality of deployable members 352a-352d to assume the expanded deployed shape, as shown in FIG. 11. The plurality of deployable members 352a-352d are sized such that an overall width of the supporting framework 350 in the expanded state, measured as the longitudinal distance between the distal end 354 of the deployable member 352a and the distal end 354 of the opposing deployable member 352c, is about 2-4 times greater than the diameter of the opening 75, thereby ensuring that the graft member 80 sufficiently covers the opening 75. After deployment and positioning of the graft member 80, a suture tying device may be used to tie the first and second tethers 30 and 32 together in a manner that holds the graft member 80 adjacent to the tissue 74 and the selected anchor 20, 120 or 220.

Referring now to FIGS. 12-13, an alternative anchor 420 is shown and described. The anchor 420 comprises a plurality of deployable members 422a-422d, each having a proximal end 423 and a distal end 424. The distal ends 424 of the plurality of deployable members 422a-422d may be joined at a base 428. One or more tethers, such as first and second tethers 30 and 32 of FIGS. 1-5 (illustrated as one tether 430 in FIG. 12) may be coupled to the anchor 420, e.g., attached to the base 428 and extending proximally therefrom.

The anchor 420 comprises a delivery state in which the anchor 420 may be delivered through a suitable insertion tool, as generally described above with regard to the embodiment of FIGS. 6-7. The anchor 420, when deployed from the insertion tool, may assume the configuration shown in FIG. 12. In a next step, an expansion member, such as exemplary balloon 450, may be used to radially expand the plurality of deployable members 422a-422d into engagement with tissue 74 surrounding the opening 75. The plurality of deployable members 422a-422d then assume an expanded deployed state as shown in FIG. 13, where the plurality of deployable members 422a-422d securely engage tissue. Barbs 455 may be provided near each of the proximal ends 423, as shown in FIGS. 12-13, to promote a secure attachment. In subsequent steps, with the anchor 420 deployed securely within the opening 75, the graft member 80 above is advanced distally over the tethers towards the anchor 420, as generally described above with regard to the method of FIGS. 4-5 and FIGS. 6-7.

In any of the above-referenced embodiments, the anchors and/or supporting frameworks may comprise a bioresorbable material, such as L-lactide/caprolactone copolymers-PLC 8516 (85/15 L-Lactide/caprolactone) as well as PLC 7015 (70/30 L-Lactide/caprolactone), which are supplied by Purac Biomaterials, Gorinchem, Netherlands. Other potential bioresorbable polymers include PLGA, PLA, PGA, PLLA, and the like. Alternatively, the anchors and supporting frameworks may comprise non-resorbable materials, including but not limited to materials disclosed herein. Similarly, the graft member 80 may comprise a material that can be integrated with the surrounding tissue. In further alternatives, the graft member 80 may comprise an adhesion barrier to facilitate coupling to tissue. In a further embodiment, a magnetic arrangement may be used, with one magnet coupled to the graft member 80 and an opposing magnet coupled to the anchor to hold the graft member 80 and the anchor in proximity to each other.

Moreover, as noted above with regard to the anchor 20, any of the anchors described herein may be deployed distal to the opening 75, in which case the anchors can assume a diameter larger than the opening 75 and provide anchoring functionality just distal to the tissue 74 with the same method steps otherwise being performed as shown herein. Alternatively, an anchor may be disposed at least partially within the opening 75 and simultaneously at least partially distal to the opening 75 in any of the embodiments shown.

While the exemplary embodiments herein have illustrated the use of one or more systems for covering an opening 75 formed in the abdominal wall, the systems disclosed herein may be useful in many other procedures. Solely by way of example, the systems may be used to treat perforations in a visceral wall, such as the stomach wall. Further, the systems 20 may be used to secure a graft member to tissue for reconstructing local tissue, and the like.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A system for facilitating closure of a bodily opening, the system comprising:
   an anchor having a deployed state dimensioned for engaging tissue surrounding the opening, the anchor comprising a plurality of deployable members;
   a tether coupled to the anchor and extending proximally from the anchor;
   a graft member comprising a bore disposed therein;
   a supporting framework coupled to the graft member, the supporting framework comprising a plurality of deployable members, wherein the plurality of deployable members of the supporting framework are coupled directly to the graft member before and after deployment of the anchor, wherein the supporting framework is directly secured at one or more locations to an outer perimeter of the graft member;
   wherein the tether is dimensioned to be disposed through the bore in the graft member such that the graft member is advanced distally over the tether after deployment of the anchor within or distal to the opening.

2. The system of claim 1 wherein at least one of the plurality of deployable members of the supporting framework are elongate members.

3. The system of claim 2 wherein one or more of the elongate members are wires or filaments.

4. The system of claim 1 wherein the anchor has a delivery state.

5. The system of claim 4 wherein when the anchor is in the delivery state, the height of the anchor is greater than or equal to the width of the anchor.

6. The system of claim 5 wherein the width of the supporting framework is between 2 and 4 times greater than the diameter of the opening in which the anchor is to be deployed.

7. The system of claim 1 wherein
   the supporting framework has a height and a width; and
   wherein when the supporting framework is in a deployed state the width of the supporting framework is at least two times greater than the diameter of the opening in which the anchor is to be deployed.

8. The system of claim 1 further comprising an actuator coupled to the anchor wherein the actuator moves the anchor from a delivery state to the deployed state and wherein the actuator comprises a loop member configured to reduce a height of the anchor while increasing the width of the anchor in the deployed state.

9. The system of claim 1 wherein the deployable members of the anchor are woven together.

10. The system of claim 1 further comprising a suture or lock configured to maintain the anchor in the deployed state.

11. The system of claim 1 wherein the deployable members of the supporting framework loop over themselves to form at least one eyelet.

12. The system of claim 11 wherein the graft member is sutured to the supporting framework around at least one eyelet.

13. The system of claim 1 wherein the system is delivered through a catheter.

14. The system of claim 1 wherein at least one of: the anchor, the supporting framework, the graft member, or the tether consists of a bioresorbable material.

15. The system of claim 1 wherein the plurality of deployable members of the supporting framework comprise of a shape-memory material.

16. A method for facilitating closure of a bodily opening, the method comprising:
   providing an anchor and a tether coupled to the anchor, the tether extending proximally away from the anchor;
   deploying the anchor into engagement with tissue surrounding the opening;
   advancing a supporting framework and graft member comprising a bore distally over the tether, with the tether being disposed through the bore;
   positioning the graft member at a desired location relative to the tissue and covering the opening; and
   securing the engagement of the graft member to the anchor,
   wherein a plurality of deployable members of the supporting framework are coupled directly to the graft member before and after deployment of the anchor, and
   wherein the deployable members of the supporting framework provide a radially outward force to hold the graft member in an expanded shape.

17. The method of claim 16 wherein the anchor comprises a plurality of deployable members that are biased radially outward in a deployed state.

18. The method of claim 16 further comprising deploying the supporting framework from a delivery state to a deployment state.

19. The method of claim 18 wherein when the supporting framework is in a deployment state the width of the supporting framework is at least two times greater than the width of the opening in which the anchor is intended to be deployed.

20. The method of claim 19 wherein when the supporting framework is in a deployment state the width of the supporting framework is between two and four times greater than the width of the opening in which the anchor is intended to be deployed.

\* \* \* \* \*